United States Patent [19]
Barsky et al.

[11] Patent Number: 5,285,519
[45] Date of Patent: * Feb. 8, 1994

[54] TRANSPARENT FILM RADIANT HEAT SOURCE FOR INCUBATORS HAVING HOOK RETAINING MEANS

[75] Inventors: Barry E. Barsky, Huntingdon Valley; Joseph P. Bagnell, Southampton; Jan F. Wenstrup, Doylestown, all of Pa.

[73] Assignee: Air-Shields, Inc., Hatboro, Pa.

[*] Notice: The portion of the term of this patent subsequent to Jun. 2, 2009 has been disclaimed.

[21] Appl. No.: 847,926

[22] Filed: Mar. 6, 1992

Related U.S. Application Data

[63] Continuation-in-part of Ser. No. 561,893, Aug. 2, 1990, Pat. No. 5,119,467.

[51] Int. Cl.⁵ .......................... A61G 11/00; H05B 3/34
[52] U.S. Cl. ........................... 392/439; 219/543; 338/308; 600/22; 119/37
[58] Field of Search .............. 392/435, 438, 439, 407; 219/203, 543, 411, 405; 600/22; 237/3, 14; 236/2, 3; 119/37; 338/308, 309

[56] References Cited

U.S. PATENT DOCUMENTS

| | | |
|---|---|---|
| 1,245,829 | 11/1917 | Vance . |
| 1,565,046 | 12/1925 | Bergdoll ............................ 219/203 |
| 1,659,487 | 2/1928 | Hudson ............................. 219/203 |
| 1,721,663 | 7/1929 | Holzhauer ......................... 219/203 |
| 1,848,337 | 3/1932 | Franzen ............................ 219/203 |
| 1,916,895 | 7/1933 | Rowe ............................... 219/203 |
| 2,064,498 | 12/1936 | Shackford et al. ................. 219/203 |
| 2,358,081 | 9/1944 | Marick . |
| 2,431,673 | 12/1947 | Auger ............................... 219/203 |
| 2,523,353 | 9/1950 | Boester . |
| 2,535,393 | 12/1950 | Daugert . |
| 2,579,964 | 12/1951 | Reynolds . |
| 3,180,781 | 4/1965 | Ryan et al. . |
| 3,299,253 | 1/1967 | Lawson, Jr. . |
| 3,655,545 | 4/1972 | Gillery et al. . |
| 3,718,535 | 2/1973 | Armstrong et al. . |
| 3,858,570 | 1/1975 | Beld et al. . |
| 3,878,361 | 4/1975 | Levin et al. . |
| 3,898,427 | 8/1975 | Levin et al. . |
| 3,974,359 | 8/1976 | Orcutt et al. . |
| 4,034,740 | 7/1977 | Atherton et al. . |
| 4,206,615 | 6/1980 | Sobajima et al. . |
| 4,399,347 | 8/1983 | Schmitt ............................. 219/203 |
| 4,459,470 | 7/1984 | Shlichta et al. . |
| 4,707,586 | 11/1987 | Voss et al. . |
| 4,743,741 | 5/1988 | Ramus . |
| 4,786,783 | 11/1988 | Woodard . |
| 4,820,902 | 4/1989 | Gillery . |

FOREIGN PATENT DOCUMENTS

| | | |
|---|---|---|
| 1251540 | 12/1960 | France . |
| 2196781 | 3/1974 | France . |
| 60-106625 | 7/1985 | Japan . |
| 812871 | 5/1959 | United Kingdom . |
| 1092164 | 11/1967 | United Kingdom . |
| 1546734 | 5/1979 | United Kingdom . |

OTHER PUBLICATIONS

"The Control of Body Temperature in the Small Newborn Infant By Low-Energy Infrared Radiation", F. J. Agate, Jr. et al. Pediatrics, May 1963.
"The Golden Canopies" From Spinoff 1978, a Publication of the National Aeronautics And Space Administration, Jan. 1978, by James J. Haggerty.
"PPG: Electrically Heated Transparency Systems For Aircraft-Marine-Railroad"by PPG Industries, (date unknown-before invention reduced to practice).
"Electriclear Heated Windshield Systems" by Libby Owens Ford, 1987.
"Sierracin Cradle Warmer Model IR-11" Sierracin Corp., Medical Products Div., Brochure, (128/1B).

*Primary Examiner*—Bruce A. Reynolds
*Assistant Examiner*—John A. Jeffery
*Attorney, Agent, or Firm*—Ratner & Prestia

[57] ABSTRACT

A radiant heater in the form of an overlay for an incubator hood. The heater has an optically transparent, radiotransparent and phototherapy transparent electrically conductive coating, preferably indium tin oxide, and includes appropriate retaining hook structure for retaining the heater on an incubator hood.

27 Claims, 4 Drawing Sheets

TRANSPARENT FILM RADIANT HEAT SOURCE FOR INCUBATORS HAVING HOOK RETAINING MEANS

BACKGROUND OF THE INVENTION

Related Application

This application is a continuation-in-part of application Ser. No. 07/561,893 filed Aug. 2, 1990 and entitled TRANSPARENT FILM RADIANT HEAT SOURCE FOR USE WITH INCUBATORS now U.S. Pat. No. 5,119,467.

FIELD OF THE INVENTION

This invention relates, in general, to the treatment of infants and, more particularly, to optically transparent radiant heat sources for use with or incorporation into infant incubators to provide radiant heat to an infant being treated in an infant incubator.

DESCRIPTION OF RELATED ART

Infant incubators are used in the treatment and maintenance of weak, sickly, premature or low birth weight infants in order to maintain infant body temperature and allow the infant to develop. Infants may lose heat in four ways: through evaporation, convection, conduction and radiation. Conductive heat loss in an infant is usually considered negligible, since the mattress upon which the infant is placed is generally an excellent insulator, and, therefore, such net heat loss is small. Evaporative heat loss is dependent upon the incubator air temperature and infant skin temperature differential, as well as the relative humidity of the incubator air and the air velocity across the infant's skin. Evaporative heat loss is often referred to as insensible water loss, and can be controlled by controlling the air flow characteristics of the incubator design, the incubator air temperature, and by adding humidity to the incubator air. Convective heat loss is also a function of the incubator air temperature and infant skin temperature differential. Radiative or radiant heat loss is a function of infant skin temperature and incubator wall temperature differential. Radiant heat loss is typically the major source of heat loss, except in the very first days in the life of a very premature, very low birth weight infant, when evaporative heat loss (insensible water loss) may be greater.

The amount of heat lost by any of the ways mentioned is dependent upon incubator design and the infant's metabolism. The desired objective of an incubator environmental control system is to provide a thermal environment which will place minimum demand on the infant's metabolism to maintain body temperature at its preferred level. Typically, this state of minimum metabolic demand is assumed to be achieved when an infant's skin temperature is maintained within a prescribed normal range.

Radiant heat loss from the infant may be reduced by minimizing radiant heat loss through the walls of the incubator. This is because the primary source of radiant heat loss in an incubator is cold incubator walls. Minimization of radiant heat loss through the incubator walls can be accomplished in either of two ways. First, by increasing the wall temperature of the incubator, the temperature differential between the infant and the incubator walls may be minimized. Second, by adding radiant energy directed to the infant through the walls of the incubator, the radiant heat lost by the infant may be balanced with the heat gained from the radiant source.

Hence, radiant warming has been used to add radiant energy to the infant. In some instances, incubators, such as the one shown in U.S. Pat. No. 3,858,570 Beld et al., have been equipped with wires embedded in the hood of the incubator in order to radiate energy to the infant. Such arrangements have the disadvantage that the wires are opaque to X rays, and interfere with visual inspection of the infant. Other incubators have been equipped with a plastic hood coated with an electrically conductive material, such as shown in U.S. Pat. No. 3,878,361 Levin et al. The coatings used have heretofore not been colorless. The coatings used generally have a yellow tint. This yellow tint causes difficulty in judging bilirubin levels in an infant making visual assessment of cyanosis more difficult.

SUMMARY OF THE INVENTION

A radiant heat source overlay, constructed in accordance with the present invention, is adapted to rest on an incubator hood and includes at least one rigid, transparent sheet section having a transparent, electrically conductive coating covering a selected surface area of the rigid, transparent sheet section. The transparent, electrically conductive coating is disposed to face the incubator hood when the overlay rests on an incubator hood. Also included in this radiant heat source overlay is a layer of transparent, protective material to which the transparent, electrically conductive coating is attached. This layer of transparent, protective material is adapted to be positioned adjacent the incubator hood onto which the overlay is placed. A radiant heat source overlay, constructed in accordance with the present invention, further includes conductor means having a first end electrically and mechanically connected to the transparent, electrically conductive coating and a second end adapted for connection to an electrical power source for conducting power to the transparent, electrically conductive coating. Also included in this overlay are retaining means adapted for engagement with the incubator hood for restricting relative movement between the overlay and the incubator hood when the overlay rests on the incubator hood.

In a preferred embodiment of the present invention, the overlay includes an inclined section and a horizontal section, with at least one of the two having a pair of rigid, transparent sheets and, between the sheets, a film of transparent, plastic material having a transparent, electrically conductive coating on a surface thereof. A set of conductor units are electrically and mechanically connected to the transparent, electrically conductive coating and have a free end adapted for connection to an electrical power source. Also included in this embodiment of the invention are means for holding the inclined and horizontal sections in a fixed relationship to one another and retaining means adapted for engagement with an incubator hood on which the overlay is placed for restricting relative movement between the overlay and the incubator hood.

The electrically conductive coating, preferably indium tin oxide, is neutral in color and transparent to phototherapy wavelengths and to x-ray transmission. The radiant heat and resultant warm walls allow a high humidity level to be maintained in the incubator with greatly reduced condensation formation on the incubator walls and rainout from the incubator walls.

With the two sheets spaced apart, an air gap is formed between the two sheets. This acts as a double wall to aid heat retention for more efficient utilization of electrical energy and reduced surface temperature exposed to the operator.

In certain applications, it may be feasible to deposit the electrically conductive coating directly on the transparent plastic sheet and eliminate the use of the film of transparent, plastic material.

Yet another aspect of the present invention is the manner in which the temperature of the radiant heat source is maintained relative to the temperature of the air within the incubator hood. Electrical power is supplied to the electrically conductive coating of the radiant heat source to maintain the overlay temperature at a preset level. Although this preset temperature level is selected with regard to the desired temperature of the air within the hood, the control of the overlay temperature is independent of the control of the temperature of the air within the hood.

By incorporating the radiant heat source in an overlay for an incubator hood, the present invention can be used with incubators in service and provides flexibility in moving such an incubator overlay from one incubator to another.

DESCRIPTION OF THE PREFERRED EMBODIMENTS

Referring to FIGS. 1 through 5, preferred embodiments of a radiant heat source overlay, constructed in accordance with the present invention, include an inclined section 10 and a horizontal section 12. In this embodiment of the invention, at least one of these sections, and preferably both, has a first rigid transparent sheet 10a and 12a and a second rigid transparent sheet 10b and 12b. Transparent sheets 10a, 10b, 12a and 12b can be a suitable acrylic plastic which is optically clear and does not impede X-ray or phototherapy transmissions.

Figure 1:
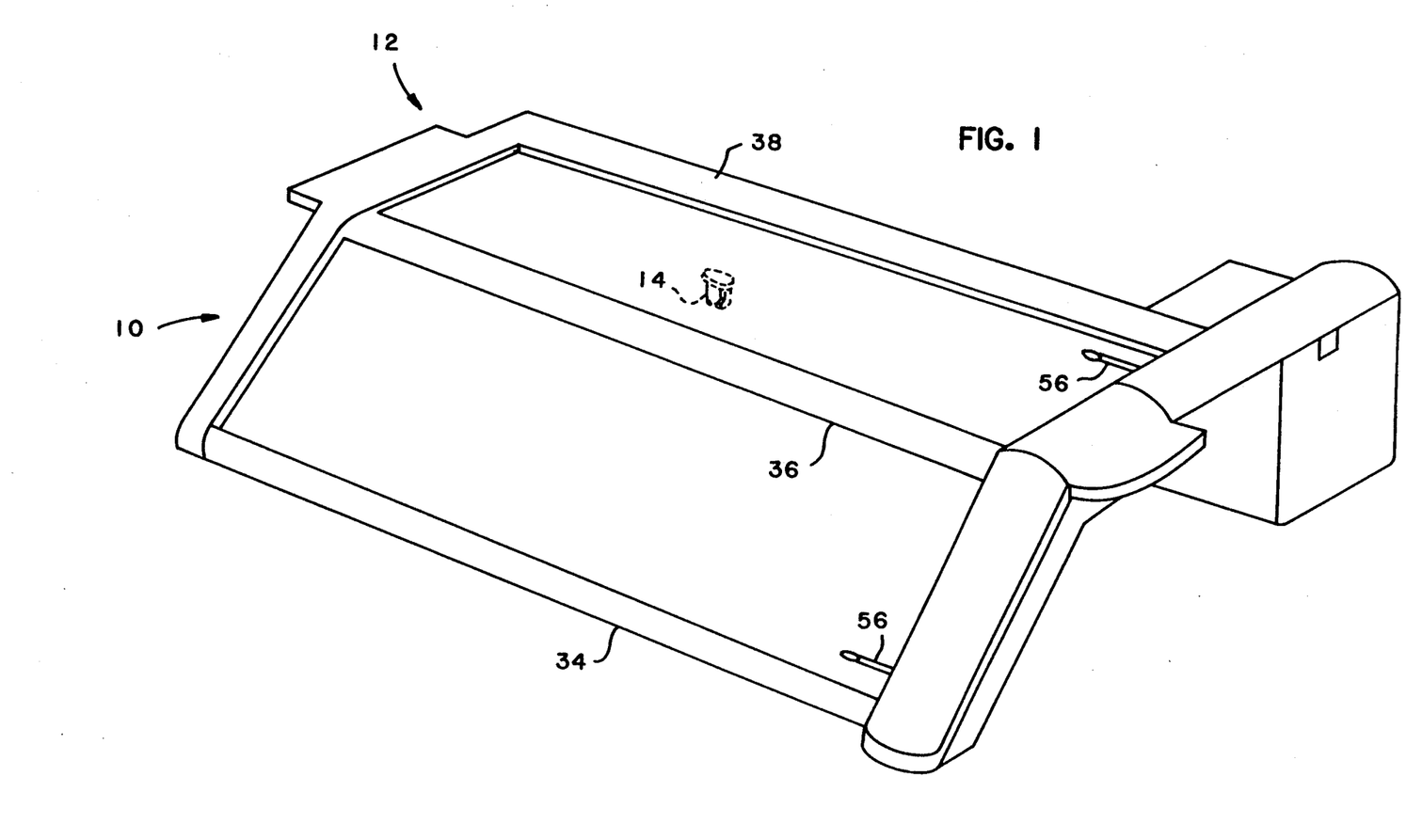
FIG. 1 is a perspective view of a first embodiment of a radiant heat source overlay constructed in accordance with the present invention.
Figure 2:
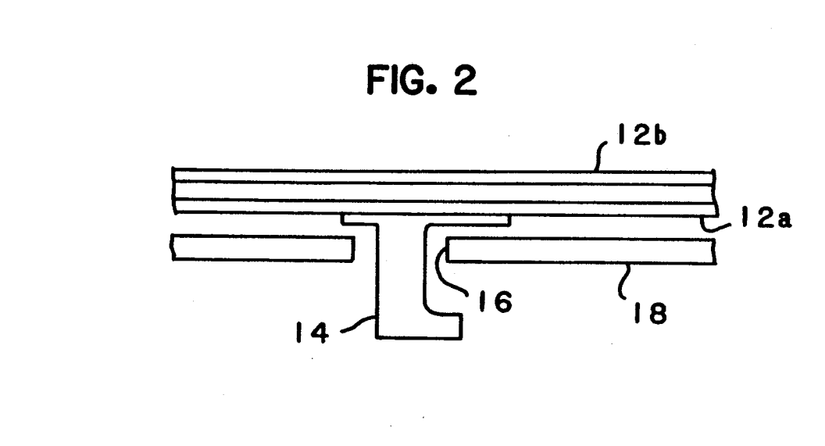
FIG. 2 is a side view, partially in cross-section, of a portion of the FIG. 1 radiant heat source overlay resting on an incubator hood.
Figure 3:
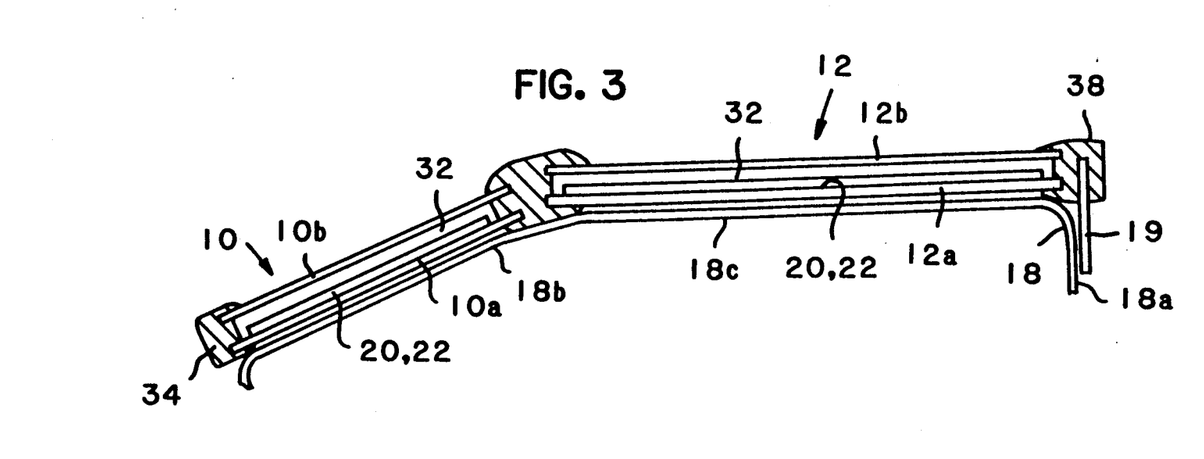
FIG. 3 is a sectional view of a second embodiment of a radiant heat source overlay constructed in accordance with the present invention resting on an incubator hood.

The embodiments of the present invention illustrated in FIGS. 1 and 3 differ in the manner by which the incubator hood overlays are retained on the incubator hood for restricting relative movement between the overlay and the incubator hood. In the embodiment of FIG. 1 and as shown most clearly in FIG. 2, the overlay has a hook member 14 which is attached to the bottom of sheet 12a of horizontal section 12 with sheet 12a positioned adjacent an incubator hood 18. Hook member 14 is arranged to pass through an instrumentation port 16 in the horizontal top of incubator hood 18. Many incubator hoods are made with such an opening in the top. If the incubator hood does not have such an opening, one can be provided very easily. Hook member 14 is designed to fit through opening 16 and also to be effective in preventing the overlay from falling off incubator hood 18 when the hood is raised as is possible with most commercially available incubators.

In the embodiment of FIG. 3, the overlay has a third section 19 which is vertical and engages the back wall of incubator hood 18. In this embodiment, vertical section 19, inclined section 10 and horizontal section 12 are adapted for positioning adjacent a vertical surface 18a, an inclined surface 18b and a horizontal surface 18c, respectively, of the incubator hood, whereby the overlay will be retained on incubator hood 18 even when the incubator hood is raised.

Figure 4:
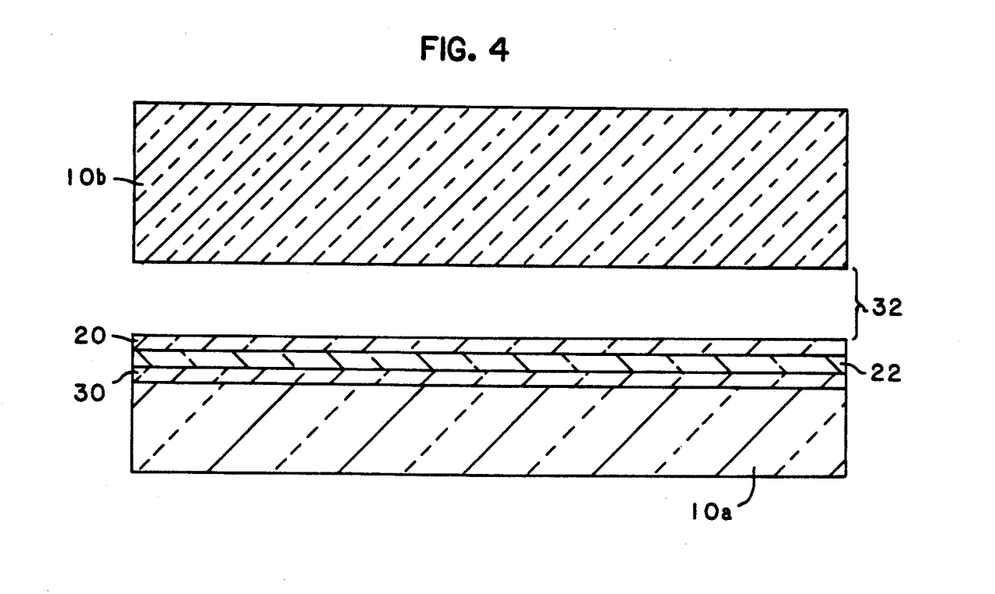
FIG. 4 is a cross-sectional view of a portion of a radiant heat source overlay constructed in accordance with the present invention.

As shown most clearly in FIG. 4, the radiant heat source overlay also includes, in one or both of sections 10 and 12, a film 20 of transparent, plastic material having a transparent, electrically conductive coating 22 on a surface thereof. Film 20 may be a polyester, such as polyethylene terephthalate or other optically clear plastic. Electrically conductive coating 22 preferably is indium tin oxide which is optically clear and colorless and is transparent to X-rays and phototherapy.

Film 20, with conductive coating 22, extends over selected surface areas of plastic sheets 10a and 12a. For the arrangement shown in FIG. 4, conductive coating 22 is between plastic sheet 10a and film 20 and is bonded to plastic sheet 10a by an adhesive layer 30 between plastic sheet 10a and conductive coating 22. As previously indicated, both inclined portion 10 and horizontal portion 12 can have a film 20 with a conductive coating 22. This is illustrated in FIG. 3.

Plastic sheets 10a and 12a, besides providing bases upon which film 20 is deposited, also serve as protective layers for film 20 and conductive coating 22 which are somewhat delicate and can be scratched or marked. Plastic sheets 10b and 12b are so positioned, relative to plastic sheets 10a and 12a, respectively, that films 20 are spaced from plastic sheets 10b and 12b to provide air gaps 32, preferably 0.080" to 0.100" wide, which act as a dead air space and thermal barrier. A plurality of longitudinal ribs 34, 36 and 38 serve to space plastic sheets 10b and 12b from plastic sheets 10a and 12a and to hold the sections together to form an overlay. Gaps 32 are sealed by suitable means along longitudinal ribs 34, 36 and 38 and at their respective ends after evacuation of the air. The overlay thus acts as an insulator, in the same way as a double wall incubator. The thermal barrier provided by gaps 32 prevents heat from being carried away from plastic sheets 10a and 12a by conduction. Further, since the spaces between sheets 10a and 10b and between sheets 12a and 12b are sealed, films 20 and conductive coatings 22 are well protected.

Figure 3A:
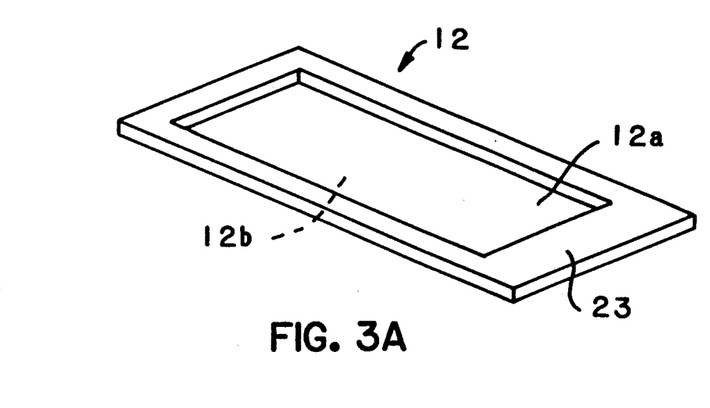
FIG. 3A is a perspective view of a preferred assembly of a radiant heater section of a radiant heat source overlay constructed in accordance with the present invention.

As shown by FIG. 3A, inclined section 10 and horizontal section 12 can be arranged as a unit, generally similar to multi-pane window assemblies which are commercially available. When so arranged, the radiant heater section is slid into two of the longitudinal ribs and held in position with suitable hardware which fastens the ends of the radiant heater section to the frame of the overlay. In particular, sheets 12a and 12b are held spaced apart by a frame 23, the longitudinal edges of which are received in ribs 36 and 38 and the end edges of which receive fasteners by which frame 23 is secured to the frame of the overlay.

It should be understood that a single wall version of the present invention also can be formed from two or more sections. For example, the overlay sections can be arranged without air gaps with film 20 and conductive coating 22 applied to plastic sheets 10b and 12b. If a protective layer is needed for film 20 and conductive coating 22, a transparent layer of silicon dioxide can be used in which case adhesive layer 30 is not necessary because silicon dioxide adheres well.

Figure 5:
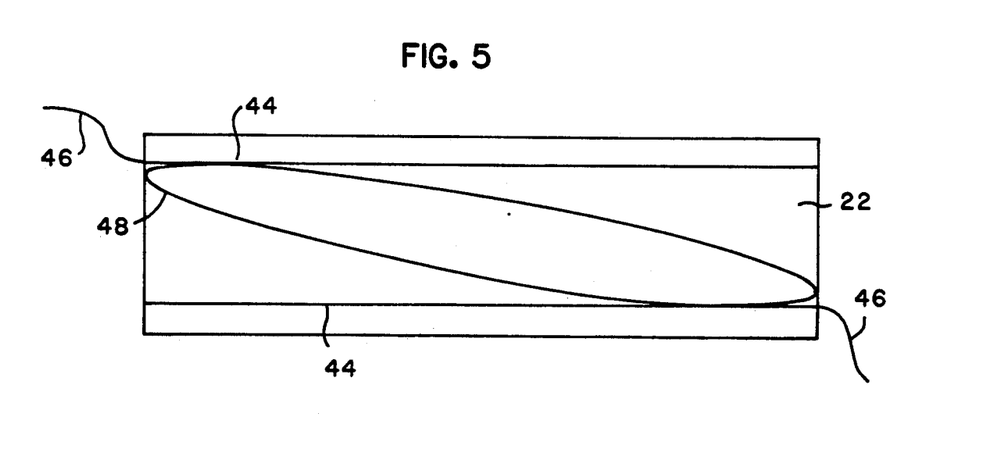
FIG. 5 is a plan view of one section of a radiant heat source overlay constructed in accordance with the present invention.

FIG. 5 is a plan view of one portion of an overlay having a radiant heat source according to the present invention. As shown by FIG. 5, each such portion has a set of conductor units with each conductor unit composed of a bus bar 44 and a lead wire 46. Each bus bar 44 extends along an edge of conductive coating 22 and is electrically and mechanically attached to the conductive coating. Each lead wire 46 extends from an end of a bus bar and has a free end adapted for connection to an electrical power source. Bus bars 44 are high conductivity/low resistance elements which deliver power to conductive coating 22. Lead wires 46 are preferably attached at opposite ends, and most preferably at opposite corners, of a rectangular shaped conductive coating 22 such as the one illustrated in FIG. 5. Due to power losses along the lengths of bus bars 44 and conductive coating 22, maximum radiation occurs along a line between the connections of lead wires 46 to bus bars 44. Radiation output decreases as one moves farther from this line. Hence, curves of constant radiation output occur. One such constant radiation output curve is identified by reference numeral 48 in FIG. 5. Radiation output outside of this curve is lower than radiation output inside the curve. This radiation gradient is minimized by locating lead wires 46 at opposite corners of the rectangular conductive coating because this configuration produces a longer and larger curve 48 and thus a more uniform pattern of radiation than what would be produced by locating both lead wires at one end of the rectangle.

Among the reasons for arranging an overlay in accordance with the present invention as multiple radiant heat sources instead of a single, shaped heat source, is that manufacturing constraints make it easier to produce a multi-part radiant heater than one large radiant heater, especially when the overlay is arranged as a double wall unit. Also, safety and control considerations may dictate the use of a multi-part radiant heater.

The disposition of conductive coating 22 is determined, primarily, by the assembly of the radiant heat source of the invention. In order to provide both physical protection and protection against chemical attack to the conductive coating as soon as possible, it is the conductive coating which is bonded to the single transparent sheet in single wall embodiments of the present invention or to one of the two transparent sheets in double wall embodiments of the present invention.

Conductive coating 22 can be applied directly to one or more of the acrylic sheets, but the process is costly. The direct application produces acceptable results, but due to cost, the previously described method, namely applying electrically conductive coating 22 to polyester film 20 and then bonding the coated film to the acrylic sheet is preferred. If the conductive coating is applied directly to the acrylic sheet, adhesive layer 24 and polyester film 20 may be eliminated.

The second reason for arranging the radiant heat source in two or more parts is that the resistance between the bus bars, and, therefore, the voltage needed to energize a radiant heater, varies directly with the distance between the bus bars. Therefore, as the radiant heater becomes larger, the voltage which is required becomes greater. General safety considerations make it desirable that the voltage remain as low as possible, and, therefore, it is desirable to use separate, smaller radiant heaters instead of one large radiant heater.

Also, by using smaller, separate radiant heaters, each one, having separate conductor units, may be separately controlled.

Figure 6:
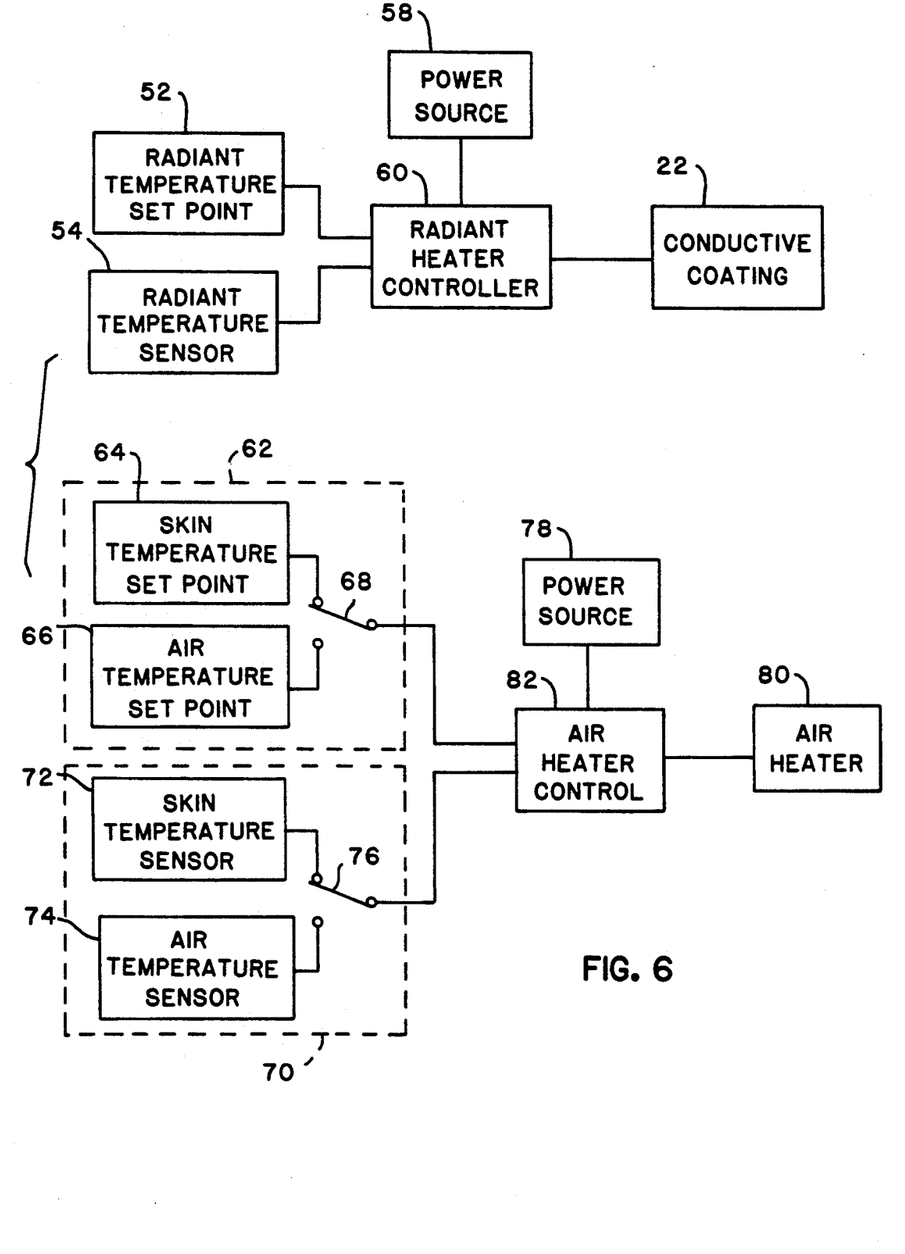
FIG. 6 is a block diagram of the controls of an air heater in an incubator and a radiant heat source overlay of the present invention.

FIG. 6 is a block diagram which shows how the temperature within the hood of an incubator can be controlled when a radiant heat source overlay, constructed in accordance with the present invention, is placed on the incubator hood. To control the radiant heat source, the control system includes means 52 for supplying a first signal representative of the desired temperature of any of the transparent sheets. Such means may include a conventional temperature setting circuit composed of a ladder network or a potentiometer arrangement. The control system also include means 54 for sensing the temperature of the transparent sheet and for supplying a second signal representative of the temperature of the transparent sheet. Such means may include a thermometer of conventional construction and operation and identified by reference numeral 56 in FIG. 1. When the radiant heat source is incorporated in a double wall arrangement, the temperature sensor may be placed in the gap between the two walls but in contact with the outer transparent sheet.

The control system further includes a first power source 58 which supplies electrical power to conductive coating 22 which, in turn, heats the transparent sheet. Power source 58 may be a conventional incubator power supply.

The amount of power supplied by power source 58 to conductive coating 22 is controlled by means 60 which are responsive to the first signal, representative of the desired transparent sheet temperature, and the second signal, representative of the actual transparent sheet temperature. Means 60 typically include a differential amplifier arrangement which develops an output representative of the difference between the desired temperature and the actual temperature and this output is used to regulate the amount of power needed to heat the transparent sheet to the desired temperature.

The control system of FIG. 6 also controls the temperature of the air circulated into the hood from the base. The arrangement shown in FIG. 6 for serving this function is fairly standard for commercially available incubators and includes means 62 for supplying a third signal representative of the desired temperature of either the skin of an infant within the hood or the air within the hood. Such means may include conventional temperature setting circuits composed of a ladder network or a potentiometer arrangement with one, identified by reference numeral 64, setting skin temperature and the other, represented by reference numeral 66, setting the air temperature. A switch 68 serves to select one of these two settings upon which control of the air temperature is based.

Also included in the control system are means 70 for sensing the actual temperature of the skin of an infant within the hood and the actual temperature of the air within the hood and for supplying a fourth signal representative of either the actual skin temperature or the actual air temperature. Such means may include a conventional skin temperature probe, represented by reference numeral 72, a conventional thermometer, represented by reference numeral 74, and a switch 76 for selecting between the outputs from the skin temperature probe and the thermometer.

The control system further includes a second power source 78 which supplies electrical power to an air heater 80, typically located in the base of the incubator. Power source 78 may be a conventional incubator power supply. Air heater 80 also may be of conventional construction and operation.

The amount of power supplied by power source 78 to air heater 80 is controlled by means 82 which are responsive to the third signal, representative of the desired skin temperature or the desired air temperature and the fourth signal, representative of the actual skin temperature or the actual air temperature. Means 82 typically include a differential amplifier arrangement which develops an output representative of the difference between the desired temperature of the selected parameter and the actual temperature of the selected parameter and this output is used to regulate the amount of power needed to heat the air to the desired air temperature or to a level sufficient to develop the desired skin temperature.

Although the radiant heat source and the air heater are separately controlled, the settings of the control parameters for each of the two should be considered together. For example, the radiant heater set point should not be so great that the heat radiated from the radiant heater adversely affects the infant. It should be remembered that, for the arrangement of the control system shown in FIG. 6, the radiant heater is not controlled by either the infant's skin temperature or the temperature of the air within the hood, so that setting the radiant heater temperature too high can affect the infant adversely because the monitored parameter has no effect of the power supplied to the radiant heater.

EXPERIMENTAL RESULTS

Two sets of tests were performed to determine the effectiveness of the radiant heating overlay in aiding heat retention in an Isolette {Isolette is a registered trademark of Air-Shields, Inc.} Model C100 single wall incubator. The results were compared against control experiments using Isolette single and double wall incubators without radiant heaters.

The first set of tests was performed with an ambient temperature of 20° C. This temperature was selected because it is reasonably extreme and would aid in producing quantifiable, comprehensible results. Further, the ambient incubator temperature differentials were such that efficacy of the radiant heater as a determinant in reducing condensation due to high incubator humidity could be observed. Each incubator was set for an internal air temperature of 37° C. Case A was the single wall incubator; Case B was the double wall incubator; and Case C was the single wall incubator with the radiant heater overlay.

In each incubator was placed a SAM VI simulator in which the surface and core temperatures were measured. Air temperature at mattress level was measured at five points around the mattress. The mattress was tilted during the tests to discover the effect of radiant heating during Fowler and Trendelenberg positions (the Fowler position is with the infant's head raised above the feet, Trendelenberg position is feet raised above the head). The results of these tests are shown in Table 1.

TABLE 1

|  | Case A Single Wall | Case B Double Wall | Case C Single wall With Heater |
|---|---|---|---|
| Mattress Level | | | |
| Center Mattress | 37.1° C. | 36.7° C. | 37.2° C. |
| Uniformity | 0.4° C. | 0.3° C. | 0.2° C. |
| SAM VI Skin | 34.9° C. | 36.1° C. | 37.4° C. |
| SAM VI Core | 34.7° C. | 35.6° C. | 37.3° C. |
| Mattress Tilted Fowler | | | |
| Center Mattress | 36.6° C. | 36.2° C. | 37.6° C. |
| Uniformity | 0.4° C. | 1.4° C. | 0.2° C. |
| SAM VI Skin | 34.7° C. | 35.3° C. | 37.7° C. |
| SAM VI Core | 34.7° C. | 35.7° C. | 37.5° C. |
| Trendelenberg | | | |
| Center Mattress | 35.3° C. | 34.1° C. | 37.3° C. |
| Uniformity | 0.6° C. | 1.1° C. | 0.3° C. |
| SAM VI Skin | 34.4° C. | 35.1° C. | 37.7° C. |
| SAM VI Core | 34.2° C. | 35.2° C. | 37.7° C. |
| Humidity Observations | | | |
| 80% Relative Humidity | Heavy condensation & heavy rainout over most internal areas | Condensation in corners, right side, & upper hood rainout near corners | Condensation in corners, light condensation in main access panel |
| Test Conditions | Set Point-37° C. Ambient Temperature-20.1° C. average Test Unit-Isolette C100 incubator Hood Heater (case C)-overlay with 3 separate heaters @ 100 ohms/in² at surface temp set point of 46.5° C. SAM VI-simulator with a surface-to-mass ratio equivalent to a 1 kilogram infant | | |

The tests revealed that mattress temperature uniformity was much better in the incubator with the radiant heater overlay than in those incubators without the heater. With the mattress flat, uniformity in Case C was 0.2° C. as compared to 0.3° C. for Case B and 0.4° C. in Case A. A desirable value for mattress uniformity is considered to be 0.5° C., which all three incubators met with the mattress flat. In the Trendelenberg position, mattress uniformity was 0.6° C., 1.1° C., and 0.3° C. for Cases A, B, and C respectively. In the Fowler position, the mattress uniformity was 0.4° C., 1.4° C., and 0.2° C. for Cases A, B, and C respectively. Thus, only the incubator equipped with the radiant heater (Case C) performed satisfactorily in the Trendelenberg position test, and Case C clearly out-performed the other incubators in both the Fowler position test and in the test with the mattress flat.

The SAM VI skin and core temperatures did not reach the set temperature of 37° C. in Cases A and B during the 19 hour test duration. In Case C, SAM VI skin temperature reached 37° C. in approximately 5 hours. SAM VI core temperature reached 37° C. in 6 hours, 24 minutes. After reaching set temperatures, the SAM VI skin and core temperatures fluctuated above and below set temperatures, indicating that thermal equilibrium had been reached.

With 80% relative humidity, Case A (single walled incubator) showed heavy condensation and heavy rainout over most internal areas. Case B (double walled incubator) showed condensation in the corners and on the upper hood, and rainout near the corners of the hood. Case C (single walled incubator including the radiant heater overlay of the present invention) showed noticeable condensation in the corners of the hood and light condensation in the main access panel, but no rainout occurred in the incubator. Thus Case C was highly acceptable.

The conditions of the second set of tests were identical to those of the first set, except that the ambient air temperature was 31° C. The results of those tests are summarized in Table 2 and need not be set out here. Summarily, those results showed trends similar to those shown by the first set of tests, though the magnitude of the differences among incubators was smaller since the test conditions were less severe. Thus, the incubator with the radiant heater overlay consistently out-performed those without the overlay.

TABLE 2

|  | Case D Single Wall | Case E Double Wall | Case F Single wall With Heater |
|---|---|---|---|
| Mattress Level |  |  |  |
| Center Mattress | 36.4° C. | 36.4° C. | 37.0° C. |
| Uniformity | 0.3° C. | 0.3° C. | 0.1° C. |
| SAM VI Skin | 35.5° C. | 36.1° C. | 37.5° C. |
| SAM VI Core | 35.2° C. | 35.9° C. | 37.1° C. |
| Mattress Tilted Fowler |  |  |  |
| Center Mattress | 35.5° C. | 36.0° C. | 37.1° C. |
| Uniformity | 1.1° C. | 0.8° C. | 0.6° C. |
| SAM VI Skin | 34.8° C. |  | 38.1° C. |
| SAM VI Core | 35.1° C. |  | 37.8° C. |
| Trendelenberg |  |  |  |
| Center Mattress | 35.4° C. | 35.3° C. | 37.2° C. |
| Uniformity | 0.4° C. | 0.4° C. | 0.6° C. |
| SAM VI Skin | 35.0° C. |  | 38.1° C. |
| SAM VI Core | 35.0° C. |  | 38.0° C. |
| Humidity Observations |  |  |  |
| 80% Relative Humidity | Condensation, rainout, vision obscured in area around front panel | Condensation at sides and front panel | No condensation observed |
| Test Conditions | Set Point-37° C. Ambient Temperature-31° C. average Test Unit-Isolette C100 incubator Hood Heater (case F)-overlay with 3 separate heaters @ 100 ohms/in² at surface temp set point of 52° C. SAM VI-simulator with a surface-to-mass ratio equivalent to a one kilogram infant |  |  |

It is understood that various other modifications will be apparent to and can be readily made by those skilled in the art without departing from the spirit and scope of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A radiant heat source overlay for an incubator hood comprising:
   an inclined section;
   a horizontal section;
   at least one of said inclined and said horizontal sections including:
   (a) a first rigid, transparent sheet,
   (b) a second rigid, transparent sheet,
   (c) a film of transparent, plastic material having a transparent, electrically conductive coating on a surface thereof, said film disposed between said first and said second rigid, transparent sheets, and
   (d) a set of conductor units electrically and mechanically connected to said transparent, electrically conductive coating with each of said conductor units having a free end adapted for connection to an electrical power source;
   means for holding said inclined an horizontal sections in a fixed relationship to one another; and
   retaining means adapted for engagement with an incubator hood on which said overlay is placed for restricting relative movement between said overlay and said incubator hood.

2. A radiant heat source overlay for an incubator hood according to claim 1 wherein:
   (a) said first and said second rigid, transparent sheets are spaced apart to form an air gap,
   (b) said first rigid, transparent sheet is adapted for positioning adjacent said incubator hood, and
   (c) said film of transparent, plastic material is on said first rigid, transparent sheet.

3. A radiant heat source overlay for an incubator hood according to claim 2 wherein both of said inclined and said horizontal sections include:
   (a) said first rigid, transparent sheet,
   (b) said second rigid, transparent sheet,
   (c) said film of transparent, plastic material,
   (d) said set of conductor units, and
   (e) a frame for spacing apart said first and said second rigid transparent sheets and with which said first and said second rigid, transparent sheets form a multi-sheet assembly.

4. A radiant heat source overlay for an incubator hood according to claim 3 wherein said holding means include a plurality of longitudinal ribs which receive said frames of said inclined and said horizontal sections.

5. A radiant heat source overlay for an incubator hood according to claim 2 further including:
   (a) a vertical section, and
   (b) means for holding said vertical and said horizontal sections in a fixed relationship to one another,
   said vertical, said inclined and said horizontal sections adapted for positioning adjacent a vertical surface, an inclined surface and a horizontal surface, respectively, of said incubator hood.

6. A radiant heat source overlay for an incubator hood according to claim 2 wherein said retaining means include a hook member adapted to engage an opening in said incubator hood.

7. A radiant heat source overlay for an incubator hood according to claim 6 wherein said hook member is fixed to said horizontal section and is adapted to engage an opening in a horizontal surface of said incubator hood.

8. An incubator comprising:
   a base;
   a hood mounted on said base; and
   a radiant heat source overlay resting on said hood and having:
   (a) an inclined section,
   (b) a horizontal section, at least one of said inclined and said horizontal sections including:
   (1) a first rigid, transparent sheet,
   (2) a second rigid, transparent sheet, (3) a film of transparent, plastic material having a transparent, electrically conductive coating on a surface thereof, said film disposed between said first and said second rigid, transparent sheets, and (4) a set of conductor units electrically and mechanically connected to said transparent, electrically conductive coating with each of said conductor units having a free end adapted for connection to an electrical power source, (c) means for holding said inclined and said horizontal sections in a fixed relationship to one another, and (d) retaining means adapted for engagement with an incubator hood on which said overlay is placed for restricting relative movement between said overlay and said incubator hood.

9. An incubator according to claim 8 wherein:
(a) said first and said second rigid, transparent sheets are spaced apart to form an air gap,
(b) said first rigid, transparent sheet is positioned adjacent said incubator hood, and
(c) said film of transparent, plastic material is on said first rigid, transparent sheet.

10. An incubator according to claim 9 wherein said retaining means include a hook member engaging an opening in said incubator hood.

11. An incubator according to claim 10 wherein said hook member is fixed to said horizontal section and engages an opening in a horizontal surface of said incubator hood.

12. A radiant heat source overlay for an incubator hood comprising:
an inclined section;
a horizontal section;
at least one of said inclined and said horizontal sections including:
(a) a first rigid, transparent sheet,
(b) a second rigid, transparent sheet,
(c) a transparent, electrically conductive coating disposed between said first and said second rigid, transparent sheets, and
(d) a set of conductor units electrically and mechanically connected to said transparent, electrically conductive coating with each of said conductor units having a free end adapted for connection to an electrical power source;
means for holding said inclined and said horizontal sections in a fixed relationship to one another; and
retaining means adapted for engagement with an incubator hood on which said overlay is placed for restricting relative movement between said overlay and said incubator hood.

13. A radiant heat source overlay for an incubator hood according to claim 12 wherein:
(a) said first and said second rigid, transparent sheets are spaced apart to form an air gap,
(b) said first rigid, transparent sheet is adapted for positioning adjacent said incubator hood, and
(c) said transparent, electrically conductive coating is on said first rigid, transparent sheet.

14. A radiant heat source overlay for an incubator hood according to claim 13 wherein said retaining means include a hook member adapted to engage an opening in said incubator hood.

15. A radiant heat source overlay for an incubator hood according to claim 14 wherein said hook member is fixed to said horizontal section and is adapted to engage an opening in a horizontal surface of said incubator hood.

16. A radiant heat source overlay for an incubator hood comprising:
a plurality of rigid, transparent sheet sections joined together into a shape adapted to rest on an incubator hood;
a transparent, electrically conductive coating covering selected surface areas of said rigid, transparent sheet sections and facing said incubator hood when said overlay rests on said incubator hood;
conductor means having a first end electrically and mechanically connected to said transparent, electrically conductive coating and a second end adapted for connection to an electrical power source for conducting electrical power to said transparent, electrically conductive coating; and
retaining means adapted for engagement with said incubator hood for restricting relative movement between said overlay and said incubator hood when said overlay rests on said incubator hood.

17. A radiant heat source overlay for an incubator hood according to claim 16 wherein:
(a) each of said rigid, transparent sheet sections includes upper and lower transparent sheets which are spaced apart to form an air gap,
(b) said lower rigid transparent sheet of each of said rigid, transparent sections is adapted for positioning adjacent said incubator hood, and
(c) and each of said lower transparent sheets has a transparent, electrically conductive coating.

18. A radiant heat source overlay for an incubator hood according to claim 17 wherein said retaining means include a hook member adapted to engage an opening in said incubator hood.

19. A radiant heat source overlay for an incubator hood according to claim 18 wherein one of said rigid transparent sheet sections is horizontal and said hook member is fixed to said horizontal section and is adapted to engage an opening in a horizontal surface of said incubator hood.

20. A radiant heat source overlay for an incubator hood according to claim 17 wherein each of said rigid, transparent sheet sections further includes a frame for spacing apart said upper and lower transparent sheets and with which said upper and lower transparent sheets form a multi-sheet assembly.

21. An incubator comprising:
a base;
a hood mounted on said base; and
a radiant heat source overlay resting on said hood and having:
(a) a rigid, transparent sheet,
(b) a transparent, electrically conductive coating positioned between said rigid, transparent sheet and said incubator hood with said transparent, electrically conductive coating facing said incubator hood,
(c) a layer of transparent, protective material to which said transparent, electrically conductive coating is attached, said layer of transparent, protective material positioned adjacent said incubator hood,
(d) a set of conductor units electrically and mechanically connected to said transparent, electrically conductive coating with each of said conductor units having a free end adapted for connection to an electrical power source, and (e) retaining means adapted for engagement with an incubator hood on which said overlay is placed for restricting relative movement between said overlay and said incubator hood.

22. An incubator according to claim 21 further including a film of transparent, plastic material onto which said transparent, electrically conductive coating is coated with said transparent, electrically conductive coating between said film of transparent, plastic material and said layer of transparent, protective material.

23. An incubator according to claim 22 wherein said layer of transparent, protective material is a second rigid, transparent sheet.

24. An incubator according to claim 23 wherein said rigid, transparent sheets are spaced apart to form an air gap between said rigid, transparent sheets.

25. An incubator according to claim 24 wherein said retaining means include a hook member engaging an opening in said incubator hood.

26. An incubator according to claim 25 wherein said hook member is fixed to said second rigid, transparent sheet and engages an opening in a horizontal surface of said incubator hood.

27. An incubator according to claim 22 wherein said layer of transparent, protective material is silicon dioxide.

* * * * *

UNITED STATES PATENT AND TRADEMARK OFFICE
CERTIFICATE OF CORRECTION

PATENT NO. : 5,285,519
DATED : February 8, 1994
INVENTOR(S) : Barry E. Barsky, et al.

It is certified that error appears in the above-indentified patent and that said Letters Patent is hereby corrected as shown below:

Claim 1, column 10, line 12, delete "an" and insert therefor --and said--

Claim 8, column 10, lines 65-66, the words "at least one of said inclined and said horizontal sections including:" begin a new paragraph on a new line Signed and Sealed this Twentieth Day of September, 1994

Attest:

BRUCE LEHMAN

Attesting Officer

Commissioner of Patents and Trademarks